(12) United States Patent
Gidekel

(10) Patent No.: US 10,190,181 B2
(45) Date of Patent: Jan. 29, 2019

(54) BIO-NEMATOCIDE

(71) Applicant: Manuel Gidekel, Santiago (CL)

(72) Inventor: Manuel Gidekel, Santiago (CL)

(73) Assignee: ICyT SpA (CL)

( * ) Notice: Subject to any disclaimer, the term of this patent is extended or adjusted under 35 U.S.C. 154(b) by 243 days.

(21) Appl. No.: 15/289,103

(22) Filed: Oct. 7, 2016

(65) Prior Publication Data

US 2017/0335414 A1    Nov. 23, 2017

Related U.S. Application Data

(63) Continuation-in-part of application No. 14/120,777, filed on Jun. 26, 2014, now Pat. No. 9,491,950.

(51) Int. Cl.
| | | |
|---|---|---|
| *A61K 36/00* | (2006.01) | |
| *C12R 1/02* | (2006.01) | |
| *A01N 63/02* | (2006.01) | |
| *C12N 1/20* | (2006.01) | |
| *C12R 1/01* | (2006.01) | |
| *B27K 3/00* | (2006.01) | |
| *A01N 63/00* | (2006.01) | |
| *C12R 1/00* | (2006.01) | |
| *A01N 25/00* | (2006.01) | |

(52) U.S. Cl.
CPC ............... *C12R 1/02* (2013.01); *A01N 63/02* (2013.01); *C12N 1/20* (2013.01); *C12R 1/01* (2013.01); *A01N 25/00* (2013.01); *A01N 63/00* (2013.01); *B27K 3/002* (2013.01); *C12R 1/00* (2013.01)

(58) Field of Classification Search
CPC ....................................................... A61K 36/00
USPC ....................................................... 424/725
See application file for complete search history.

(56) References Cited

U.S. PATENT DOCUMENTS 9,491,950 B2 *    11/2016    Gidekel ................. A01N 63/02

* cited by examiner

*Primary Examiner* — Michael V Meller
(74) *Attorney, Agent, or Firm* — John Dodds

(57) ABSTRACT

The present invention provides for a bio-nematocide for repairing damage to wood and related cellulosic products caused by nematodes.

1 Claim, 25 Drawing Sheets

Specification includes a Sequence Listing.

```
>Gluconacetobacter malus
GTGTAGTTAAGTTTTTACAATACAAGTCGCACGATCTTTTCGGGTTTAGTGGCGGACGGGT
GAGTAACGCGTAGGGATTTATCCACGGGTGGGGAATAATTTTGGAAAACTGAAGCTAATCC
CGCATGACACCTGAGGGTCAAAGGCGCAAGTCCCCTGTGGAGAAACCTGCTTTCAATTACC
TAGTTGGGGGGTAAAGGCCTACCAAGGCAATGATCAATAGCTGGTCTGAGAGGATGATCA
CCCACACTGGACTGGGACTGAAACACGGCCCAAACTCCTACGGGAGGCAGCAGTGGGAAATATTGA
ACAATGGGCGCAAACCCTGATCCACCAATGCCGCGTGTGTGAAAAAGGTTTTCGGATTGTAA
AGCATTTTCAGCGGGGACAATGATGACGGTCCCCCGCAAAAAAACCCCGGCTAATTTCGTG
CCAGCACCCGCGGTAATACAAGAGGGGCAAGCGTTGCTCGAAATGACTGGGCGTAAAGGGC
GCGTAGGCGGTTGACACAGTAAAGTGTGAAAAAGGGTTGTGAAATTCCCAGTGTAGAGGTGAAATTCG
ATACGTGGCAACTAAAGTGTGAAAAACACCGGGGCAACCTGGCTCATGACTGACCCTGAGG
TAAATATTGGAAAAACACCGGGGCAAAGGCGGATTAAATACCCTGGTAGTCCACGCTGTAAACAATGT
CGCAAAAGCGTGGGAGCAAACAGGATTAGATACCCTGGTAGTCCACGCTGTAAACAATGT
GTGCTGAATGTTGGGTGACTTTGTCATTCAGTGTCGTATTTAACGCGATAAGCACACCGCC
TGGGGAGTACGGCCGCAAGGTTAAACTCAAAGAAATTGACGGGGCCCCACAAGCGGGG
GAGCATGTGGTTTATTTCAAAGCAACGCGCAAAAACCTTACCAGGGCTTGACATTGGGAAGG
CCGTGTCCAGAAATGGGCATTTTCTCGCAAAAAAACCTCAACCAACAGGTGCCTGCATGGT
TTGTCTCCCTCTCCGGTCCGGGAA
```

Fig. 1

| Nematode Species | Treatment | No. of nematodes/250 cm³ of soil | | Reproductive Rate 30 dpa (R)^Y | |
|---|---|---|---|---|---|
| | | Initial population (pi) | Population 30 dpa (pf) | pf/pi | % of control 30 dpa |
| *Xiphinema index* | Eagle One 10% | 396.0 | 180.0 | 0.45 a | 49.9 |
| | Vydate® L 10 L/ha | 194.0 | 72.2 | 0.37 a | 59.0 |
| | Control | 717.2 | 650.4 | 0.91 b | |
| *Helicotylenchus, Paratylenchus,* and *Pratylenchus* | Eagle One 10% | 272.5 | 113.3 | 0.42 | 38.0 |
| | Vydate® L 10 L/ha | 848.3 | 292.3 | 0.35 | 48.7 |
| | Control | 878.0 | 591.3 | 0.67 | ns |

Y is obtained by calculating *population final / population initial (Pf / Pi)*. Different letters following values in the same column indicate significant differences (p < 0.05, Fisher's Least Significant Difference Test). Values marked with ns did not present significant differences between treatments (p < 0.05).

FIG 17

| Treatment | Replicates | Helicotylenchus BA | Helicotylenchus PA | Paratylenchus BA | Paratylenchus PA | Pratylenchus ♀ BA | Pratylenchus ♀ PA | Pratylenchus ♂ BA | Pratylenchus ♂ PA | Xiphinema index BA | Xiphinema index PA | Saprophytes BA | Saprophytes PA |
|---|---|---|---|---|---|---|---|---|---|---|---|---|---|
| 0 | 1 | 0 | 0 | 594 | 345 | 18 | 30 | 21 | 3 | 29 | 43 | 786 | 1796 |
| 0 | 2 | 24 | 36 | 243 | 216 | 843 | 264 | 126 | 54 | 117 | 176 | 1362 | 1754 |
| 0 | 3 | 989 | 1203 | 145 | 711 | 27 | 82 | 0 | 6 | 577 | 528 | 502 | 1710 |
| 0 | 4 | 93 | 18 | 1083 | 162 | 12 | 24 | 0 | 12 | 1931 | 1751 | 1486 | 992 |
| 0 | 5 | 24 | 49 | 714 | 138 | 0 | 0 | 0 | 0 | 199 | 392 | 1142 | 2296 |
| 0 | 6 | 36 | 0 | 21 | 21 | 225 | 144 | 30 | 30 | 762 | 405 | 2888 | 1598 |
| 1 | 1 | 115 | 46 | 3 | 0 | 28 | 78 | 20 | 9 | 275 | 107 | 896 | 952 |
| 1 | 2 | 0 | 0 | 372 | 60 | 12 | 51 | 0 | 6 | 143 | 754 | 438 | 544 |
| 1 | 3 | 34 | 34 | 153 | 27 | 66 | 171 | 9 | 9 | 704 | 360 | 448 | 888 |
| 1 | 4 | 6 | 12 | 342 | 48 | 63 | 36 | 10 | 36 | 486 | 280 | 590 | 2456 |
| 1 | 5 | 63 | 6 | 129 | 48 | 144 | 3 | 9 | 3 | 299 | 110 | 850 | 1766 |
| 1 | 6 | 925 | 0 | 57 | 0 | 0 | 0 | 0 | 0 | 216 | 43 | 2668 | 1250 |
| 2 | 1 | 9 | 3 | 45 | 0 | 60 | 42 | 0 | 15 | 348 | 169 | 1558 | 500 |
| 2 | 2 | 6 | 12 | 54 | 0 | 984 | 133 | 114 | 15 | 9 | 70 | 514 | 470 |
| 2 | 3 | 204 | 171 | 51 | 3 | 342 | 235 | 60 | 45 | 150 | 94 | 766 | 262 |
| 2 | 4 | 711 | 462 | 24 | 90 | 66 | 619 | 3 | 123 | 262 | 50 | 438 | 344 |
| 2 | 5 | 214 | 54 | 63 | 3 | 729 | 102 | 99 | 27 | 100 | 19 | 1294 | 1490 |
| 2 | 6 | 195 | 15 | 214 | 3 | 789 | 270 | 123 | 57 | 110 | 29 | 768 | 716 |

FIG. 18

| Treatment | Initial population # $Pi$ | Final Population # $Pf$ | Population growth & $1-Pf/Pi$ |
|---|---|---|---|
| Control | 1178.5 ± 607.7 | 1646.5 ± 482.3 | 40 ± 45 |
| EAGLEONE™ Plus 1/50 (2%) | 1572.0 ± 67.9 | 1020.0 ± 42.4 | -35 ± 10 |
| EAGLEONE™ Plus 1/20 (5%) | 1533.3 ± 860 | 525.3 ± 54.2 | -66 ± 20 * |
| EAGLEONE™ Plus 1/10 (10%) | 1932 ± 512 | 481 ± 13 | -75 ± 06 * |
| Rugby | 1607.3 ± 656 | 455 ± 168.2 | -72 ± 15 * |

*All data are expressed as the average ± standard deviation. The initial (Pi) and final (Pf) populations reflect the average number of nematodes counted at all sites at the time of sampling. The Pf was determined 30 days post-treatment. Population growth was independently determined for each site, and these data were then averaged together. The final population growth is shown as a percentage of the initial population. * indicates significant differences against the control (Tukey's test, $P \leq 0.01$).

FIG. 19

SEQUENCE LISTING

```
<160> NUMBER OF SEQ ID NOS: 1

<210> SEQ ID NO 1
<211> LENGTH: 1000
<212> TYPE: DNA
<213> ORGANISM: Komagataeibacter xylinus

<400> SEQUENCE: 1
gtgtagttaa gtttttacaa tacaagtcgc acgatctttt cgggtttagt ggcggacggg     60
```

```
tgagtaacgc gtagggattt atccacgggt ggggaataat tttggaaaac tgaagctaat    120
cccgcatgac acctgagggt caaaggcgca agtcccctgt ggagaaacct gctttcaatt    180
acctagttgg gggggtaaag gcctaccaag gcaatgatca atagctggtc tgagaggatg    240
atcacccaca ctgggactga aacacggccc aaactcctac ggggaggcagc agtgggaaat    300
attgaacaat gggcgcaacc ctgatccacc aatgccgcgt gtgtgaaaaa ggttttcgga    360
ttgtaaagca ttttcagcgg ggacaatgat gacggtcccc gcaaaaaaac ccccggctaa    420
tttcgtgcca gcacccgcgg taatacaaag ggggcaagcg ttgctcgaaa tgactgggcg    480
taaagggcgc gtaggcggtt gacacagtca aatgtaaaat tcccgggttt aacctggggg    540
ctgcttttga tacgtggcaa ctaaagtgtg aaaagggtt gtgaaattcc cagtgtagag    600
gtgaaattcg taaatattgg aaaaaacacc gggggcaaag gcggcaacct ggctcatgac    660
tgaccctgag gcgcaaaagc gtggggagca aacaggatta aatacctgg tagtccacgc    720
tgtaaacaat gtgtgctgaa tgttgggtga ctttgtcatt cagtgtcgta tttaacgcga    780
taagcacacc gcctggggag tacggccgca aggttaaaac tcaaagaaat tgacgggggc    840
ccgcacaagc gggggagcat gtggtttatt tcaaagcaac gcgcaaaacc ttaccagggc    900
ttgacattgg gaaggccgtg tccagaaatg ggcattttct cgcaaaaaaa cctcaaccaa    960
caggtgcctg catggtttgt ctccctctcc ggtccgggaa                         1000
```

BIO-NEMATOCIDE

REFERENCE TO CROSS RELATED APPLICATIONS

This Continuation-In-Part Application is based on U.S. Nonprovisional patent application Ser. No. 14/120,777, filed on Jun. 26, 2014, which is incorporated herein in their entirety.

SEQUENCE LISTING

The instant application contains a Sequence Listing which has been submitted electronically and is hereby incorporated by reference in its entirety.

FIELD OF THE INVENTION

The present invention embraces a biological system that can be used as bio-repair, insecticide, termiticide and bio-additive. This invention provides a biomaterial based in a bacteria that produces cellulose from sugar derivate. The biological system increases the resistance and flexural strength and also has an insecticide effect.

BACKGROUND OF THE INVENTION

Soil termites, also known as subterranean termites, are the most destructive termites in the United States. These insects, and other related insects can cause a lot of damage and should be controlled upon discovery.

Hundreds of thousands of termites in a colony well-organized among workers, soldiers and Queens tunnel 24 hours a day through soil and into the wooden frames of houses, fences and buildings providing new sources of cellulose for the entire colony.

If left untreated, termites can destroy the entire value of a home. According to the National Pest Management Association, termites are costing Americans more than $5 billion in damage each year. This is more than fire and floods combined. Destruction is boundless, because any home, regardless of design, can offer the ideal combination of heat, moisture and food for termites. In addition, many plans for housing are not covered by insurance for such damages. Without insurance protection, serious problems in selling a house may arise. Many lenders require a termite bond before lending money to homebuyers.

SUMMARY OF THE INVENTION

The present invention provides for the first time a biological system which provides the dual function of killing termites and other wood damaging insects while also producing a by-product substance having the capability of repairing damage by termites and other insects to wood and related cellulosic products.

In a particular embodiment of the present invention, a biological system, toxic to termites, is provided which produces a means by which damage caused by termites is repaired, said means comprising a by-product produced by a modification of the bacteria of the genus *Gluconacetobacter*. Preferably, the biological system is in the form of toxic bait.

In another embodiment of the present invention, a process is provided for killing termites and other wood damaging insects and for repairing damage to wood and related cellulosic products caused by termites comprising the steps of:
  (a) Providing a modification of the bacteria of the genus *gluconacetobacter* toxic to termites and wood damaging insects, and insects family like acaridae and nematodes
  (b) Converting said bacterial modification into a bait attractive to termites and other insects as a source of food;
  (c) Allowing said bacterial modification to produce by-product ooze capable of repairing would damage by termites and other wood damaging insects.

The by-product ooze is toxic to termites and other insects and non-toxic to humans.

Summing up the summary of the present invention is:
New microbial strain PTA 121405 (ATCC)
Activity as nematocide, insecticide and repellent
For use above and below ground parts of plants
Formulation solution/liquid ready to use. Self-life>8 months
Non-toxic to humans, higher animals, bees, earthworms, Daphnia and cyanobacteria
Use in agriculture, homes and garden, institutions (hospitals, schools, etc.) and industrial facilities
As one application nematocide (1/10) at Rutgers tomatoes drastically reduce the formation of new galls and eggs when compared with a water control and chemical nematocide (done by UC Davis)
Field tests in Cabernet Sauvignon reduce the number of infective juvenile Xiphinema using Eagle One (1/20) (at University of Chile)
Field trials in peaches and citrus have demonstrated 85% control of aphids, whiteflies and thrips 10 days after application a mortality using 400 cc/ha (done by Agri-Development)
Low-cost production

BRIEF DESCRIPTION OF THE DRAWINGS

FIG. 1. shows the 16S ribosomal RNA gene sequence of *Gluconacetobacter malus*.

FIG. 17 shows a chart with the variations in Xiphinema index populations and in the collectively assessed Helicotylenchus, Paratylenchus, and Pratylenchus genera in grapevines farmed at a vineyard located in the La Pintana community (Santiago, Chile).

FIG. 18 shows a chart with the detected nematode genera. Sexes marked in yellow were those statistically evaluated in the present assays. Before Application (BA), Post-Application (PA).

FIG. 19 shows the variations in the Xiphinema index population, the primary species present in grapevines during experimental tests evaluating the efficiency of EAGLE-ONE™ Plus at two concentrations. The number of live nematodes found in 250 cm3 of soil is presented.

DETAILED DESCRIPTION OF THE INVENTION

Figure 2:
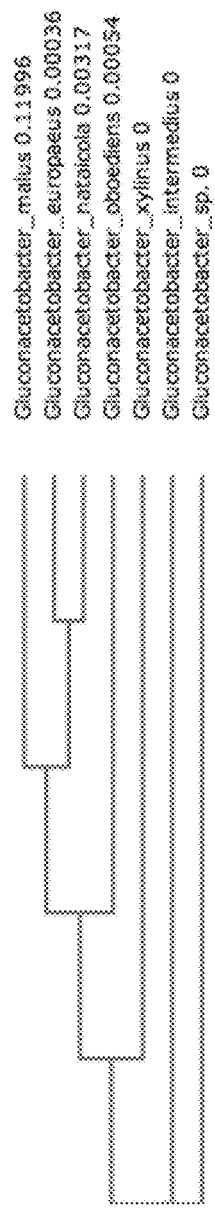
FIG. 2. illustrates the phylogenetic tree of 16S ribosomal RNA gene sequence of *Gluconacetobacter malus* with other species with high similarity.

A *Gluconacetobacter* bacterium from an apple was isolated. First, the apple was washed with distilled water and then it was crashed in 25 mL of sterile distilled water as well. The extract produced was incubated for 10 days at room temperature for the bacteria production. After this incubation, serial dilutions of the culture were done on LB agar plates and were incubated at 27-Celsius degrees for 2 days. The most diluted colonies corresponding to the white colored colonies were selected and analyzed by 16srRNA-PCR procedure using F8 forward primer (AGAGTTT-GATCCTGGCTCAG) and R1492 reverse primer (GGT-TACCTTGTTACGACTT) (Weisburg et al. 1991; Baker et al., 2003). The sequence obtained (FIG. 1) was analyzed by BLAST and had 92% of identity with *Gluconacetobacter intermedius* (gi: 594191428), *Gluconacetobacter xylinus* (gi: 359803333), *Gluconacetobacter* sp. (gi: 323482039), *Gluconacetobacter oboediens* (gi: 359803727), *Gluconacetobacter europaeus* (gi: 380292627) and *Gluconacetobacter nataicola* (gi: 343200325). So, we called our bacteria strains as *Gluconacetobacter malus*. Also, a phylogenetic tree analysis using ClustalW2-Phylogeny program was performed (FIG. 2).

An evaluation of cellulose yield was done. *G. malus* was cultured in liquid mediums using different nutrient sources (glucose and sugar derivate) for 2 weeks at 27 Celsius-degrees without shaking (static culture) to produce cellulose. A cellulose yield of 128.8 g/L, 119 g/L, 111.9 g/L, 99.8 g/L and 94.9 g/L was produced by *G. malus*. From glucose, sugar beet derivates 1, 2, 3 and 4, respectively (shown in Table 1).

TABLE 1

Cellulose yield using different nutrient sources.

| Sugar Source | Cellulose Yield (gr cellulose/ml culture) | Cellulose Yield (gr cellulose/L culture) |
|---|---|---|
| Glucose | 0.13 | 128.8 |
| Sugar Beet Molasses 1 | 0.12 | 119 |
| Sugar Beet Molasses 2 | 0.11 | 111.9 |
| Sugar Beet Molasses 3 | 0.10 | 99.8 |
| Sugar Beet Molasses 4 | 0.09 | 94.9 |

Example 1

Biological System as Bio-Repair

To test the biological system as bio-repair, physical properties of these celluloses were assayed by doing a Dynamic Mechanic Analysis (DMA). Resistance and mechanical strength of cellulose are five times more in comparison with wood-cellulose.

Figure 3:
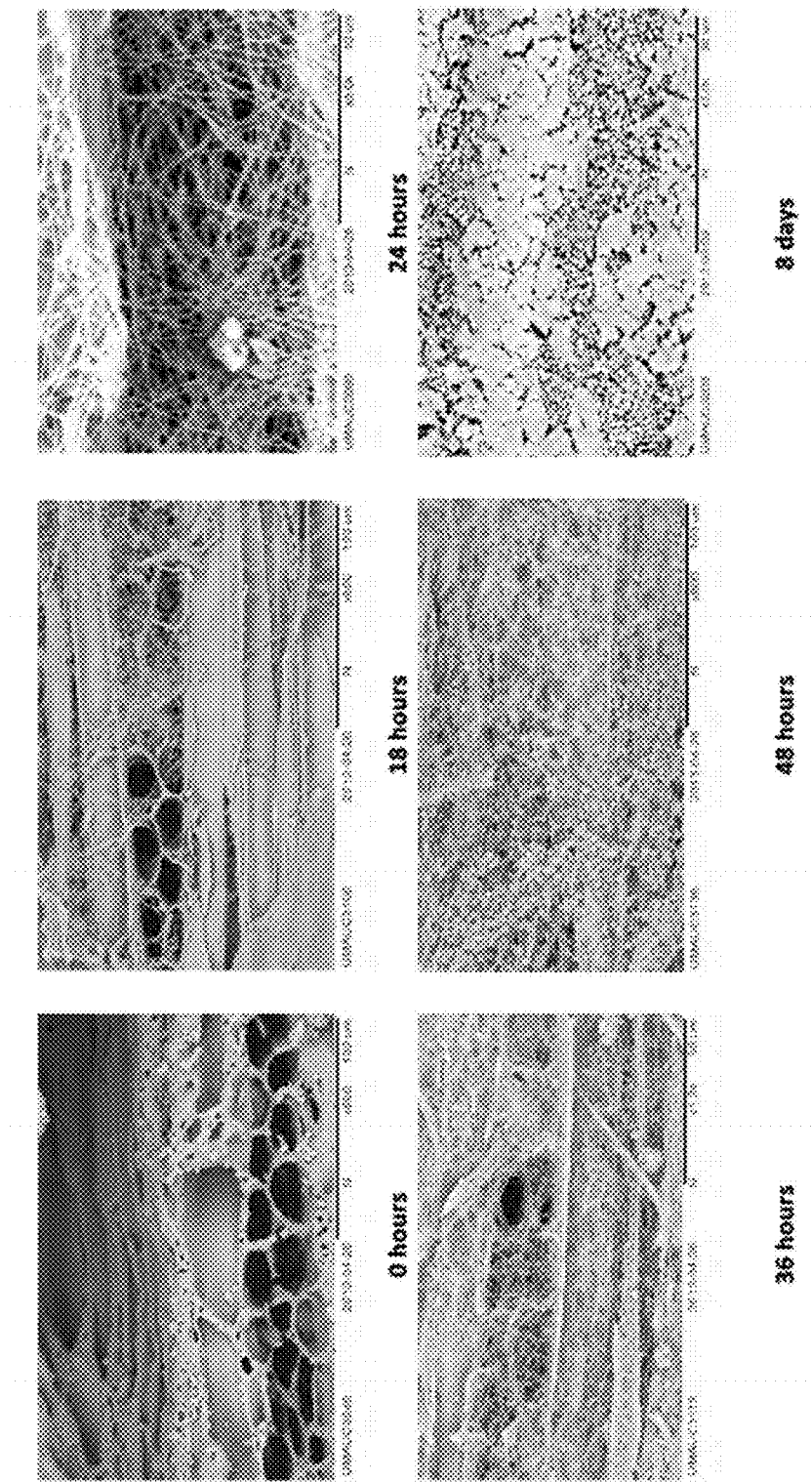
FIG. 3. shows the kinetic coverage of the cellulose adding the bacteria during the time.

Furthermore, electronic microphotographs shows how this biological system repairs and reconstitutes the damaged wood starting on the initial hours from its application to 8 days (FIG. 3). At 24 hours, a great quantity of cellulose's fibers can be shown. An efficient bio-repair process can be detected from 24 hours up to 8 days.

In USA there are 79.000.000 homes affected by termites. This biological product has a lot of advantages: is not toxic to the human, doesn't damage the environment and is a very effective as bio-repair product. It can be used as bio-repair on damaged wood's structures of homes caused by termites and other insects.

Example 2

Biological System as Insecticide

Figure 4:
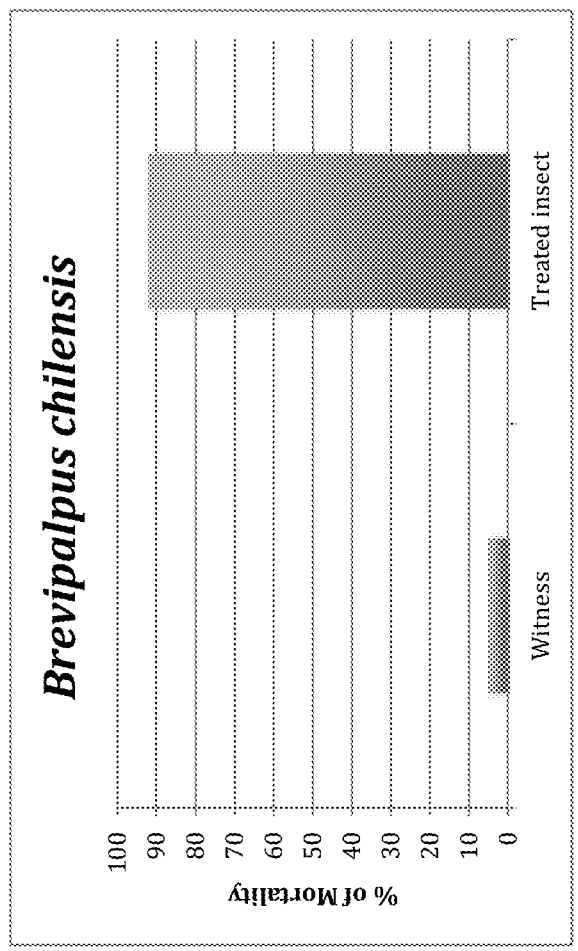
FIG. 4. shows the percentage of mortality of *Brevipalpus chilensis* with water (witness) and treated insect with culture supernatant (SN) of the bacterial cellulose culture. The SN was added to the privet leaves, not directly to the insect. After 7 days of post-treatment, the percentage of mortality was measured. This assay was performed using eggs and mobile insects. Each assay was done 10 times.

To evaluate the insecticidal effect, an aliquot of the supernatant from bacterial cellulose cultures was settled on a plate with a coleopteran to emulate the natural environmental conditions. When the coleopteran reaches the supernatant, the insect dies. Contrary to when the insect eats the bacterial cellulose. These assays were performed using *Brevipalpus chilensis* (a mite that infects vine plants). The SN was added to the privet leaves, not directly to the insect. After 7 days of post-treatment, we measured the percentage of mortality. A 92% of mortality was shown using the SN of the bacterial cellulose culture (FIG. 3). Also, the same assay was done, but using a 1/10 dilution of the SN (FIG. 4). We detected a 73% of mortality. So, the diluted SN is very effective.

Figure 5:
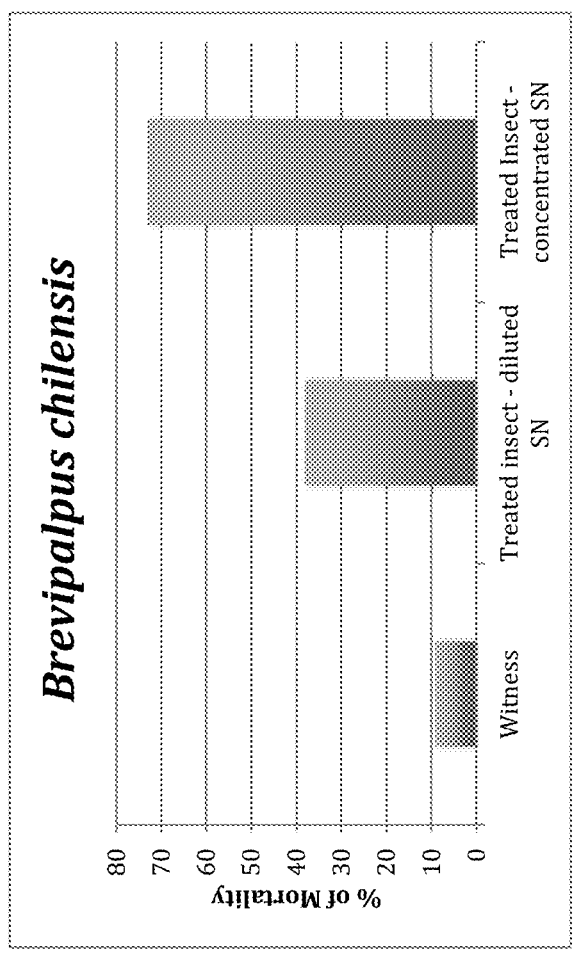
FIG. 5. Shows the percentage of mortality of *B. chilensis* using water (witness), diluted supernatant (diluted SN) and concentrated SN (direct SN of bacterial cellulose culture). The assay was done as in FIG. 3.
Figure 6:
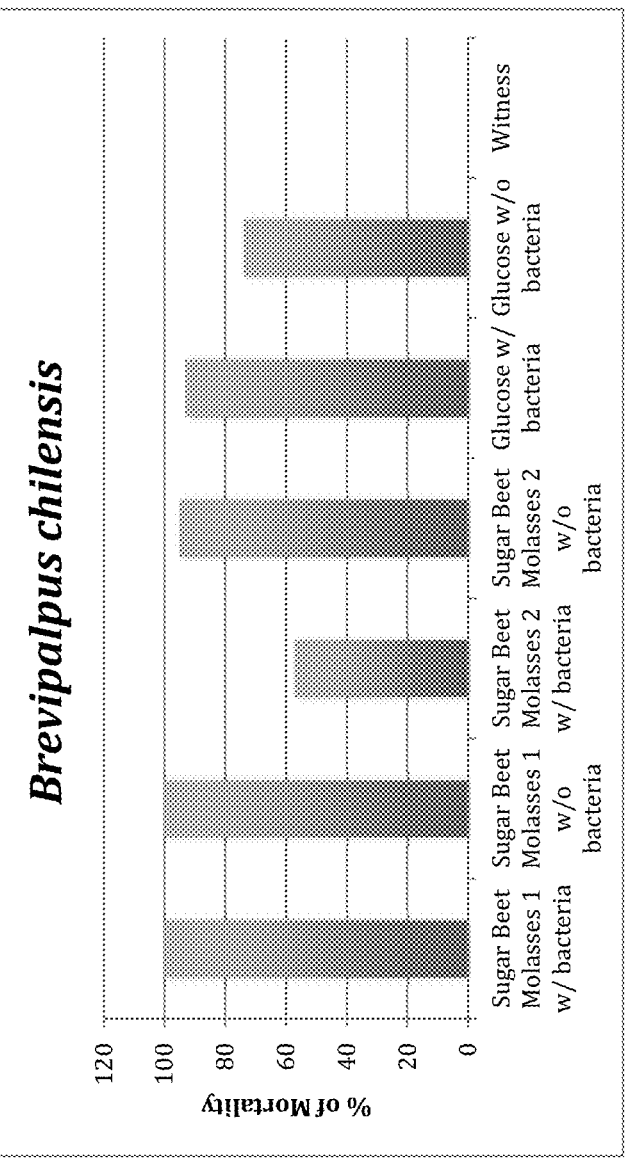
FIG. 6. shows the percentage of mortality of *B. chilensis* using supernatant (SN) of bacterial cellulose culture using different nutrient sources (sugar beet derivates 1 and 2, and glucose) with or without bacteria (treated with 0.1 N NaOH). The assay was done as in FIG. 3.

Furthermore, a similar assay was performed using SN from bacterial cellulose cultures with different nutrient source. We determined that the different SNs were effective (FIG. 5). Also, the same treatment was done with and without bacteria (SN with 0.1 N NaOH). We saw activity in both treatments. We conclude that the toxin is in the bacterial cellulose supernatant.

In the vinifera vine sprouting in early may cause tissue necrosis and death cause of outbreaks and also, dehydration rachis, pedicels and bronzing of leaves.

On the other hand, we test the insecticidal effect using 9 nematodes (Table 2). Nematodes-based termite s are phytoparasitic of a wide of vegetable cultivation like tomato and also vine plants. In this assay we use the SN (filtrated or not) of the liquid culture using Sugar Beet Derivate 1 as carbon source. All the insects die using the SN. Water added to the nematodes was used as negative control. The SN is effective against different types of insects.

TABLE 2

Insecticidal effect of Supernatant using Sugar Beet Molasses as nutrient sources

| Dilution | Filtrated | Not Filtrated | Water |
| --- | --- | --- | --- |
| 1 Supernatant/ 9 nematodes | 9 nematodes died | 9 nematodes died | 9 nematodes alive |
| 5 Supernatant/ 5 nematodes | 5 nematodes died | 5 nematodes died | 5 nematodes alive |

This biological product can be used as insecticide, mostly important as a termiticide to protect the wood structures from termites while this product is repairing the damaged wood as mentioned before. Also, can be used in the agriculture, mainly in the countries that are susceptible to insect damage by mites and other insects. This new biological compound shows a great potential to control the damage of *Brevipalpus chilensis* in our *Vitis vinifera*. The actually acaricides are not sufficient effective to control this mite.

Example 3

Biological System as Bio-Additive

The biological compound can be used in the fabrication of added-resistance laminated and agglomerated wood panels. Plywood increases over 5 times its resistance to flexion.

In 2011, the International Agency for Research on Cancer (IARC) classifies the formaldehyde as carcinogenic agent, based on epidemiologic studies of cancer in animals and humans. The new biological compound can replace the formaldehyde to a polymer that catalyzes the dry and reduces the use of matchwood for the Eco-wood formulation, using materials that aren't toxic on humans.

Evaluation of the Composition of the Present Invention (called EagleOne) as a Nematocide (performed by the University of California, Davis)

Objectives

Determine the effectiveness of EagleOne® (EO) against infective juveniles (IJs) of a) *Meloidogyne incognita*, the root knot nematode and b) *Steinernema feltiae*, an important beneficial entomopathogenic nematode.

Methods

All work was done on University of California campus in Davis, Calif., USA. Plant pathogenic nematodes were obtained from a laboratory culture maintained in the UC Davis Department of Entomology and Nematology. The beneficial nematode was obtained from Koppert Inc.

The effect of EO was tested on infective juveniles (IJs) of *M. incognita*. One nematode was added per well in a 96 cell well plate with each cell containing 200 µl of different dilutions of EO (1/1, 3/4, 1/2, 1/5, 1/10, 1/20, 1/30 and 1/40). A control cell was established using only distilled water. The treatments were incubated at 20° C. in a moist chamber (Nalgene Acrylic Desiccator Cabinet, Thermo Fisher Scientific, Waltham, Mass.) using wet paper toweling to maintain high humidity. A single nematode in a well was considered one replicate; twenty-one replicates of each treatment were made. Living and dead nematodes were counted under a microscope after 2, 4 and 24 hours and the viability of nematodes was determined using an eyelash probe. Nematodes not moving when touched with the probe were considered dead. To further confirm this, an additional test was done to determine if the nematodes would recover. After the 24 h exposure time nematodes were washed with distilled water and incubated at 20° C. for 24 h; a determination of live and dead nematodes was made as described previously. Similar procedures were followed when EO was tested on *S. feltiae* except only dilutions of 1/1, 1/2, 1/5, 1/10, 1/20 and 1/30 were used. Both experiments were repeated. However in the second *M. incognita* experiment a 48 h exposure period was added. ANOVA and Turkey's statistical test were used to analyze the data (JMP software, USA).

Results

Morality of *M. incognita*

Figure 7A:
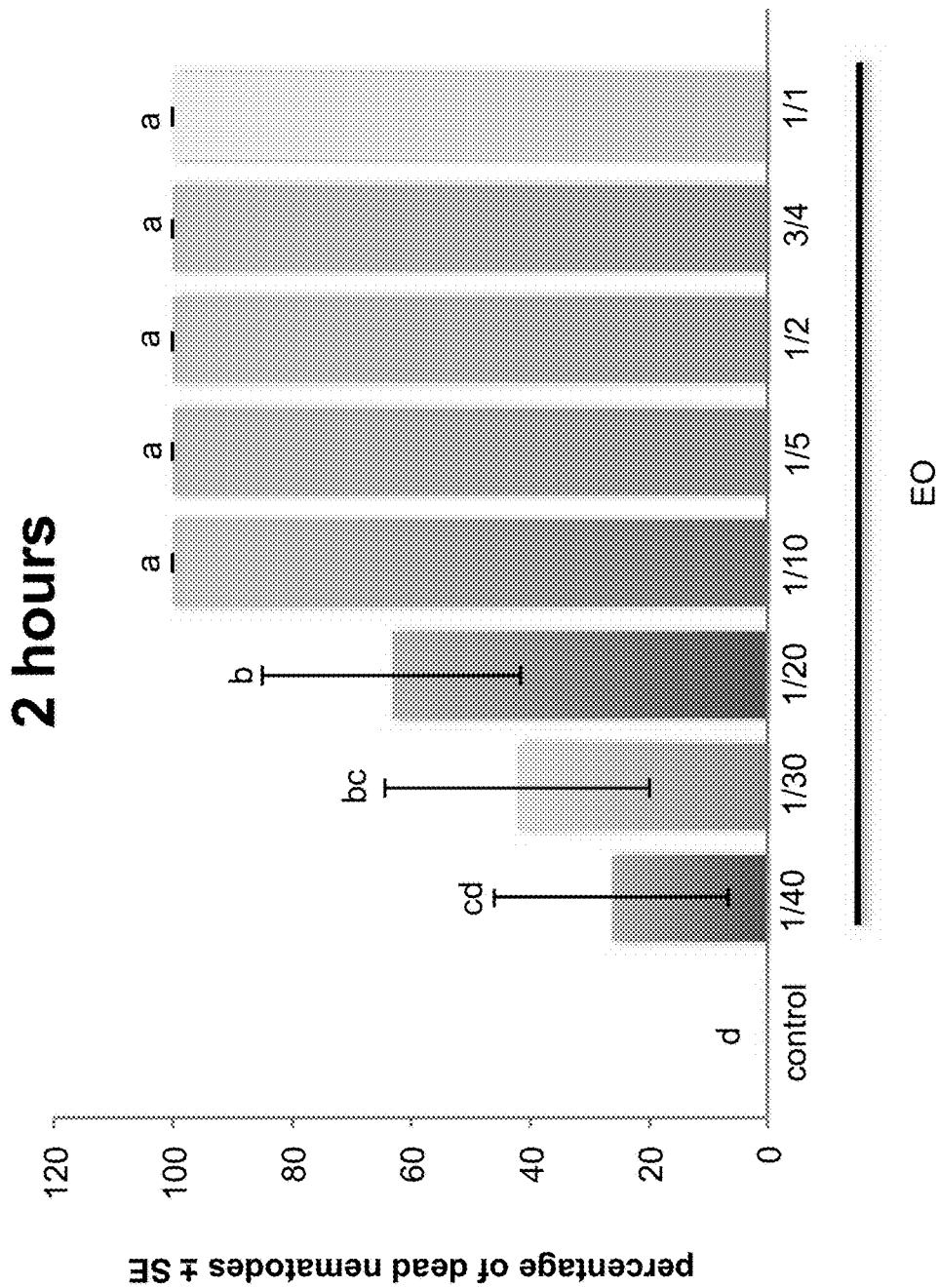
FIGS. 7A-C is a chart that shows the percent mortality (±SE) of Us of *M. incognita* using different EO dilutions after 2, 4 and 24 h exposure periods. ANOVA and Tukey's test were used to analyze the data. Means followed by the same letter are not significantly different (p-value>0.05).
Figure 7B:
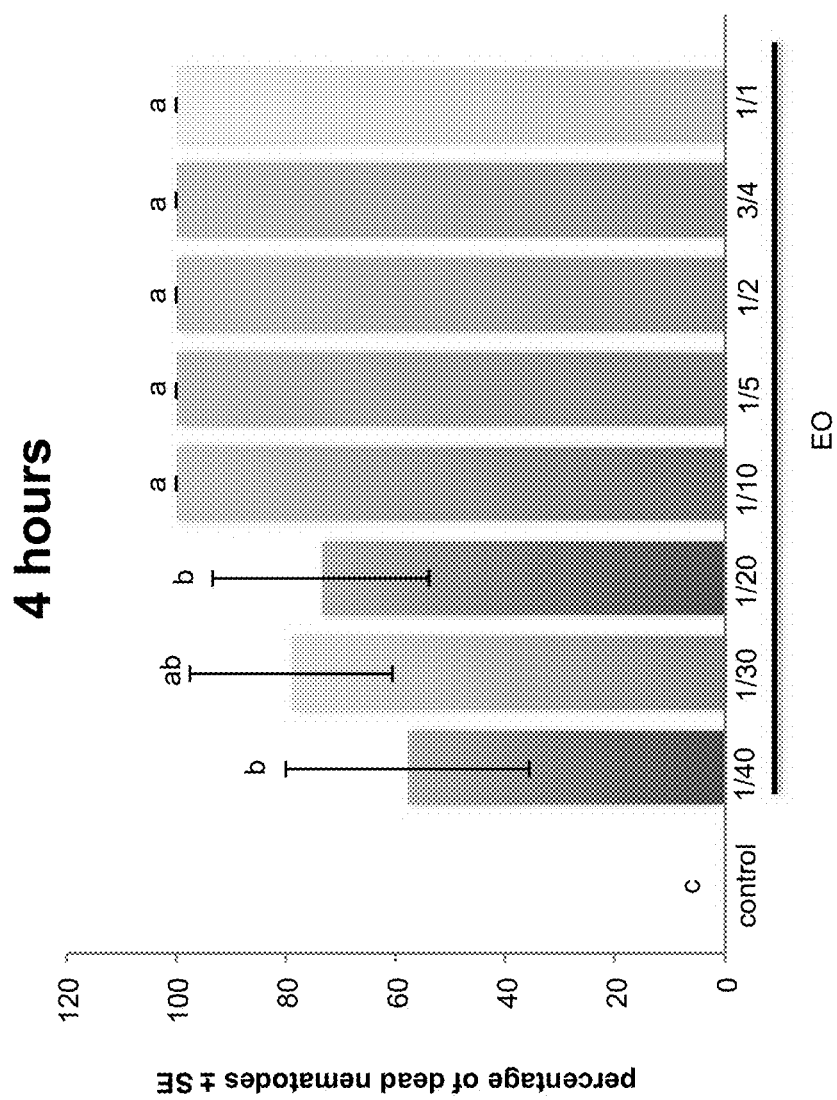
Figure 7C:
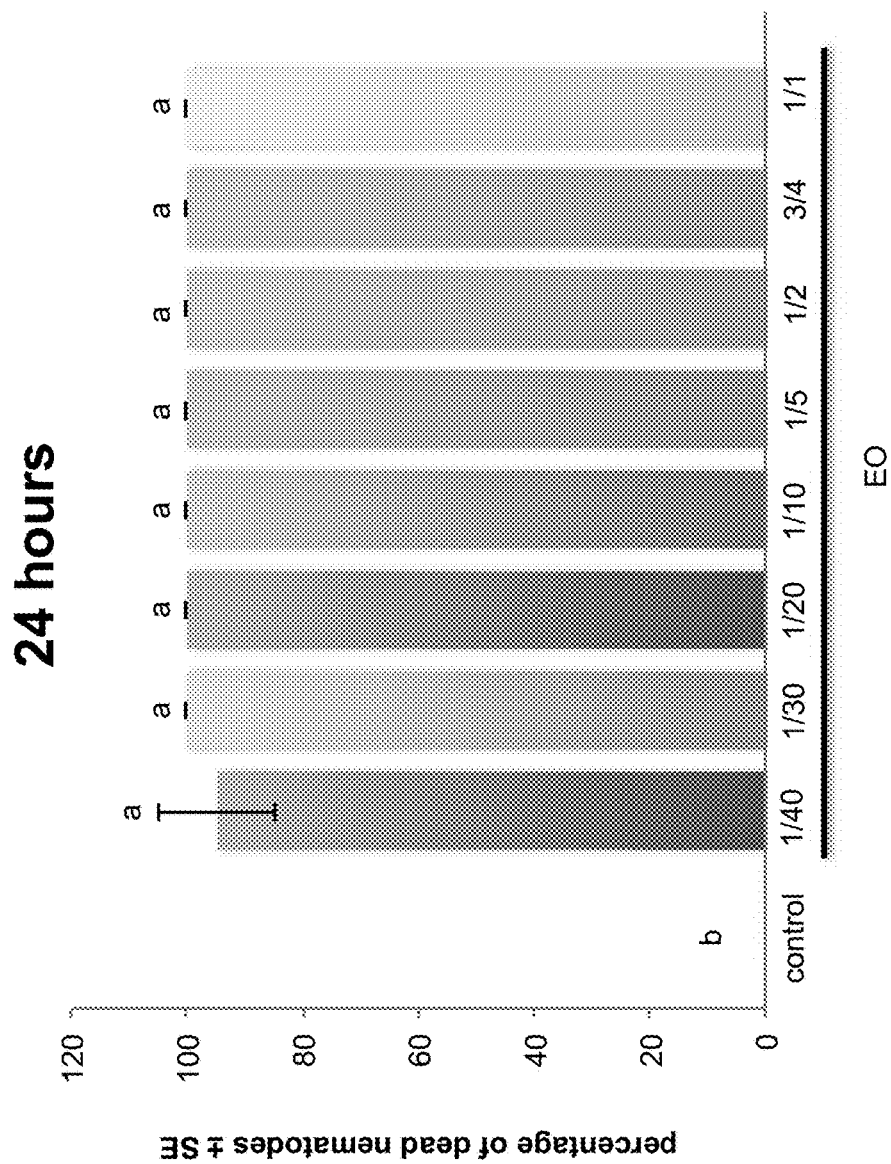
Figure 8A:
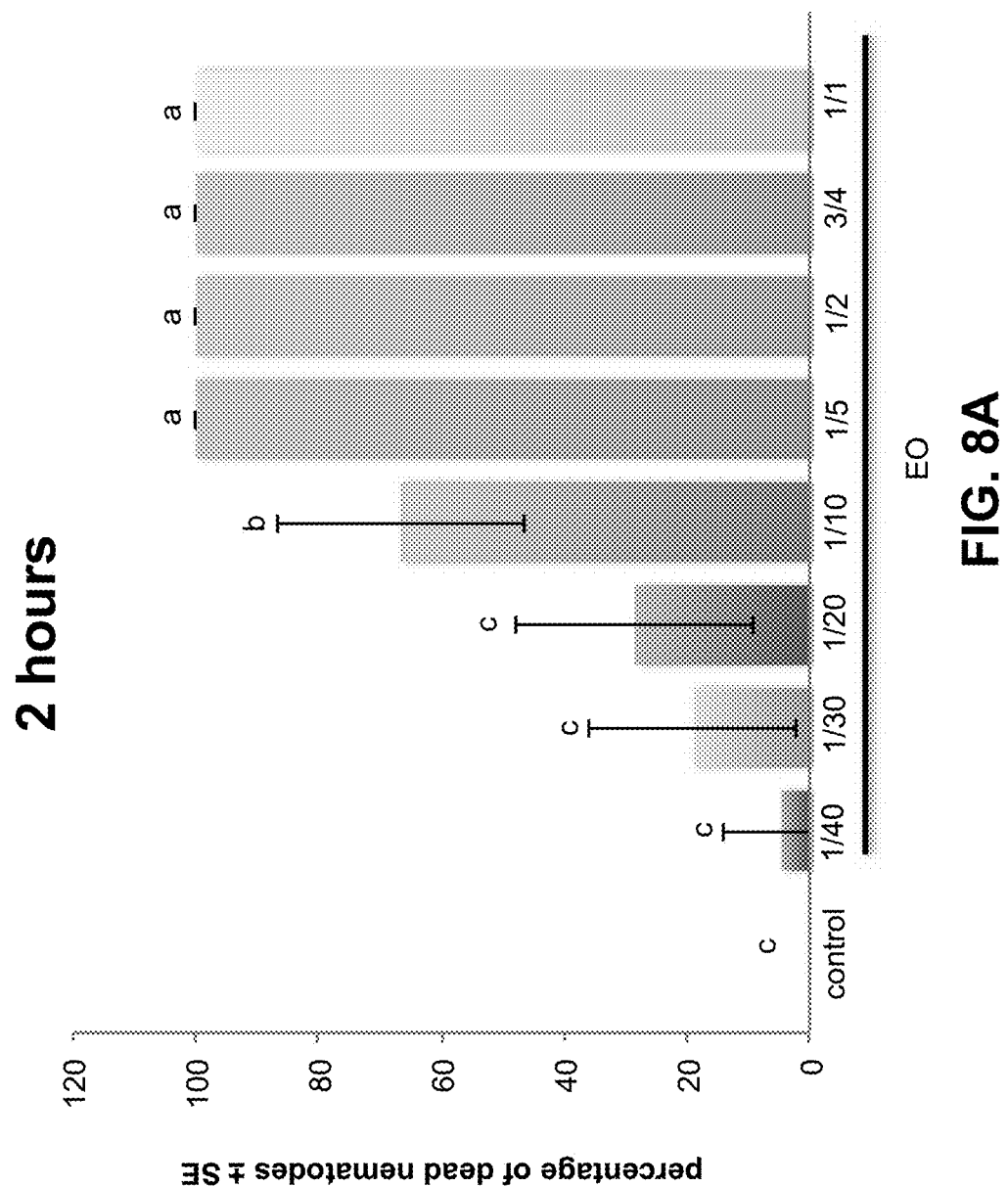
FIGS. 8A-D shows the percent mortality (±SE) of Us of *M. incognita* using different EO dilutions after 2, 4, 24 and 48 h exposure periods. ANOVA and Tukey's test were used to analyze the data. Means followed by the same letter are not significantly different (p-value>0.05).
Figure 8B:
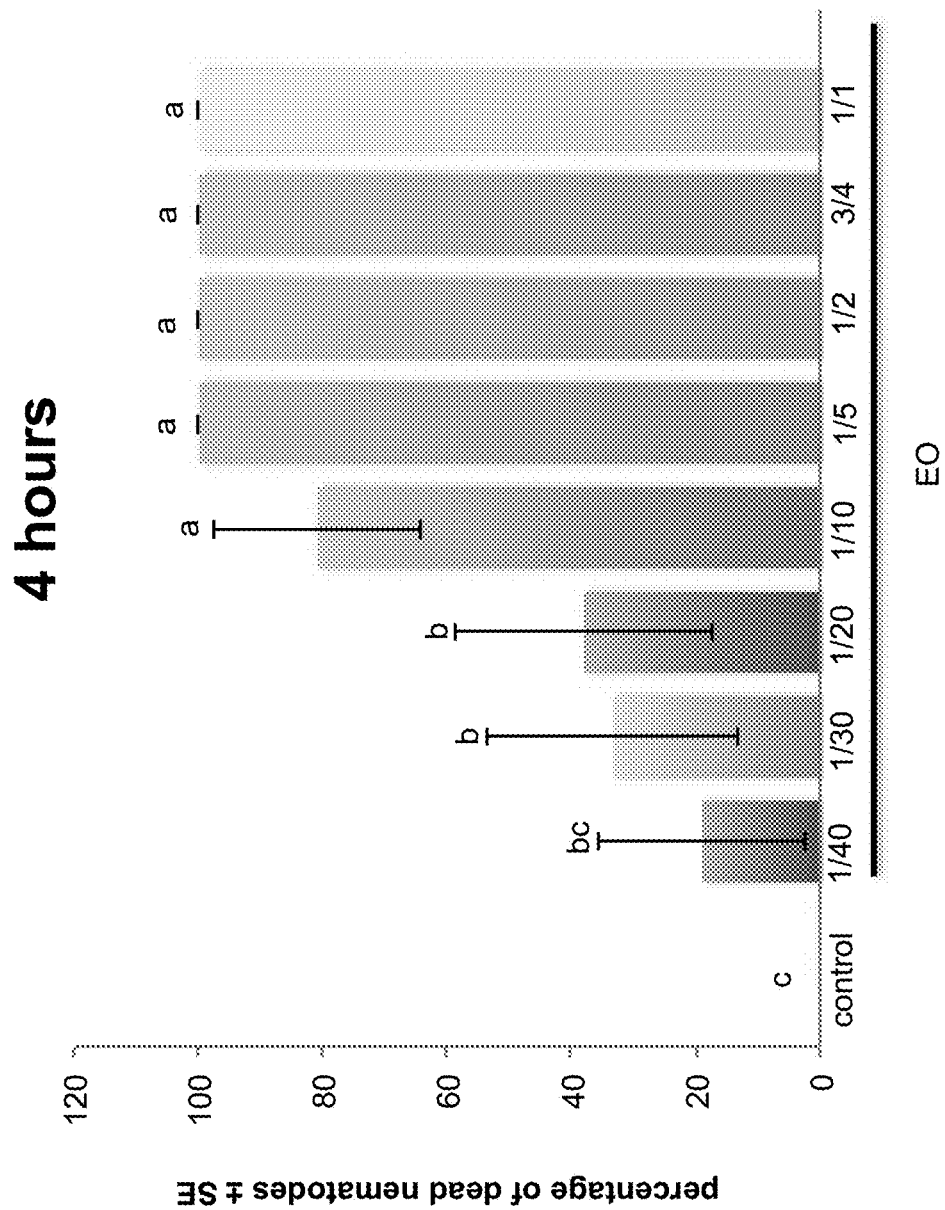
Figure 8C:
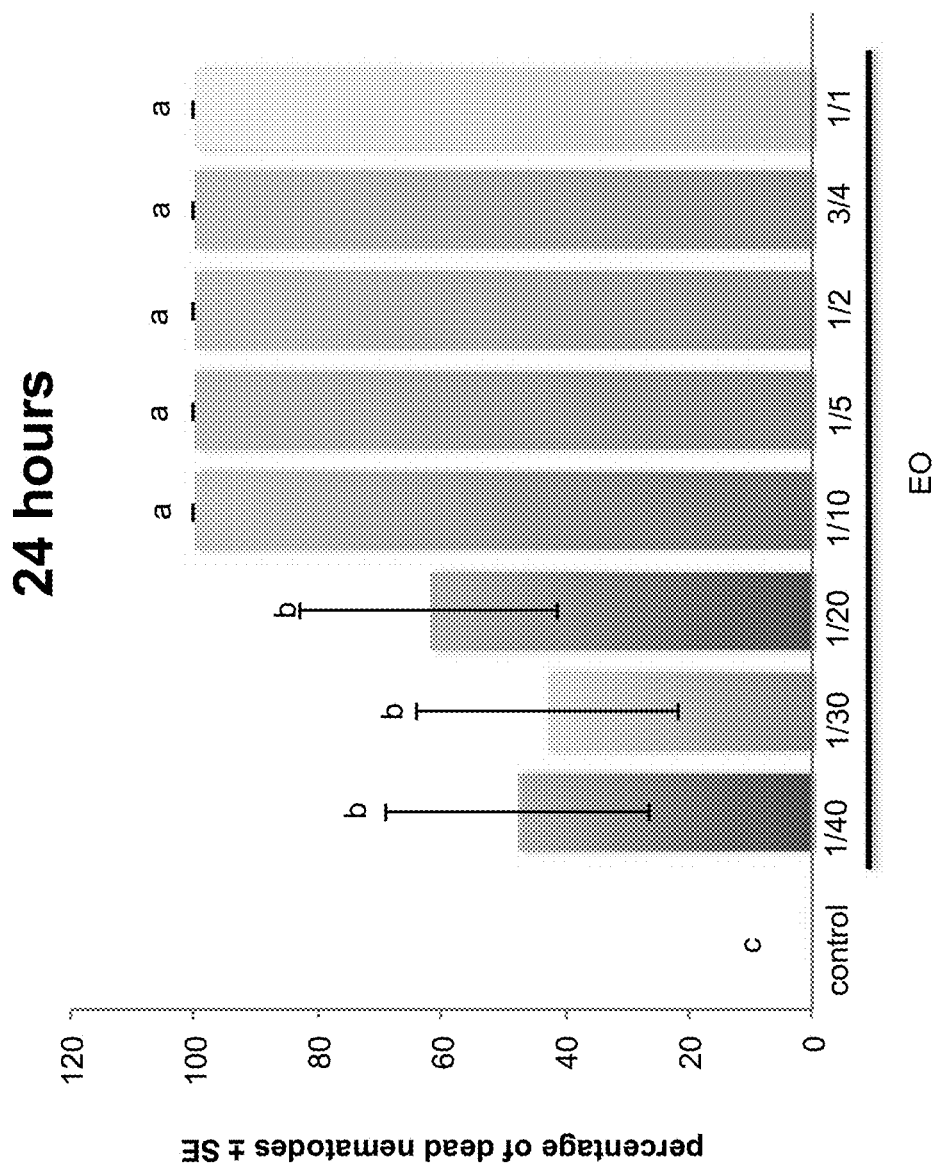
Figure 8D:
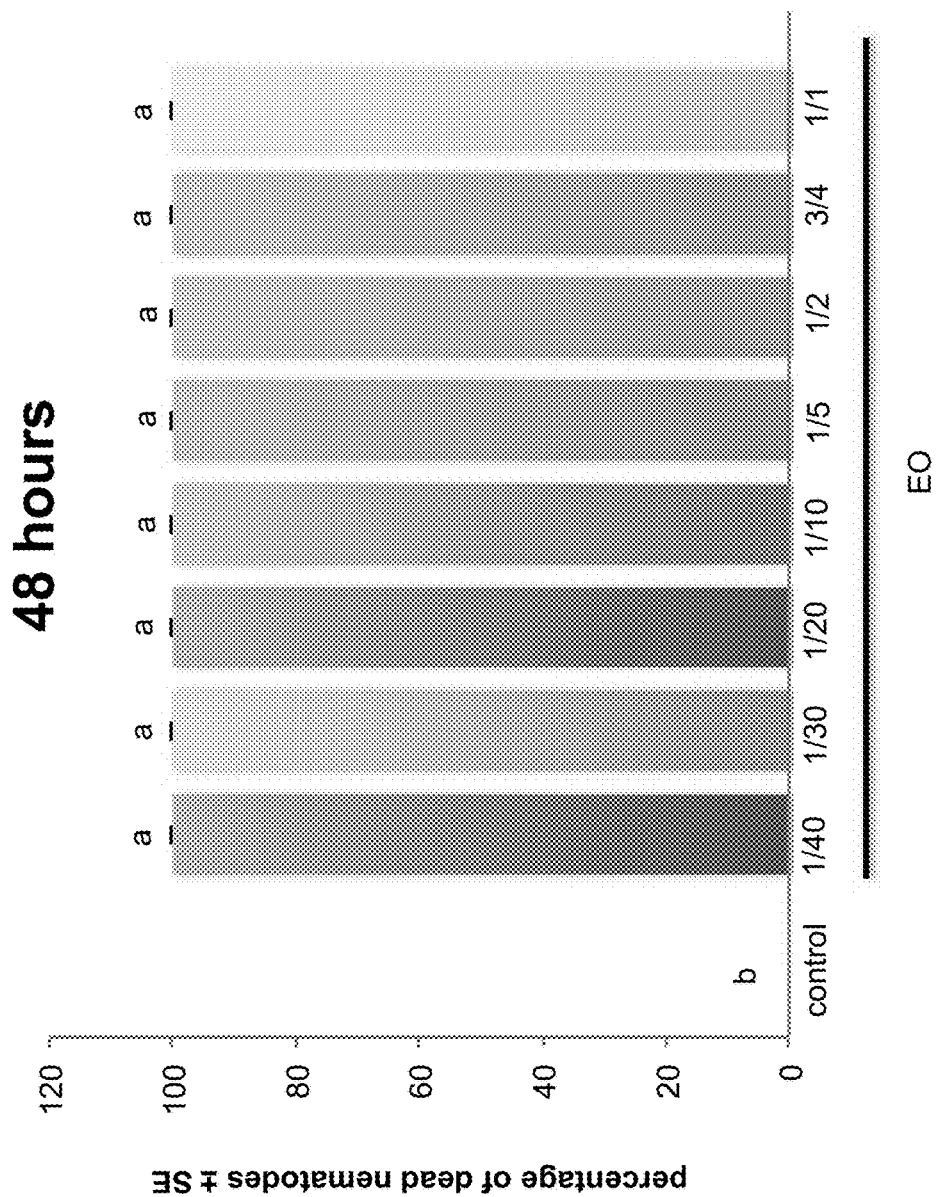
Figure 9:
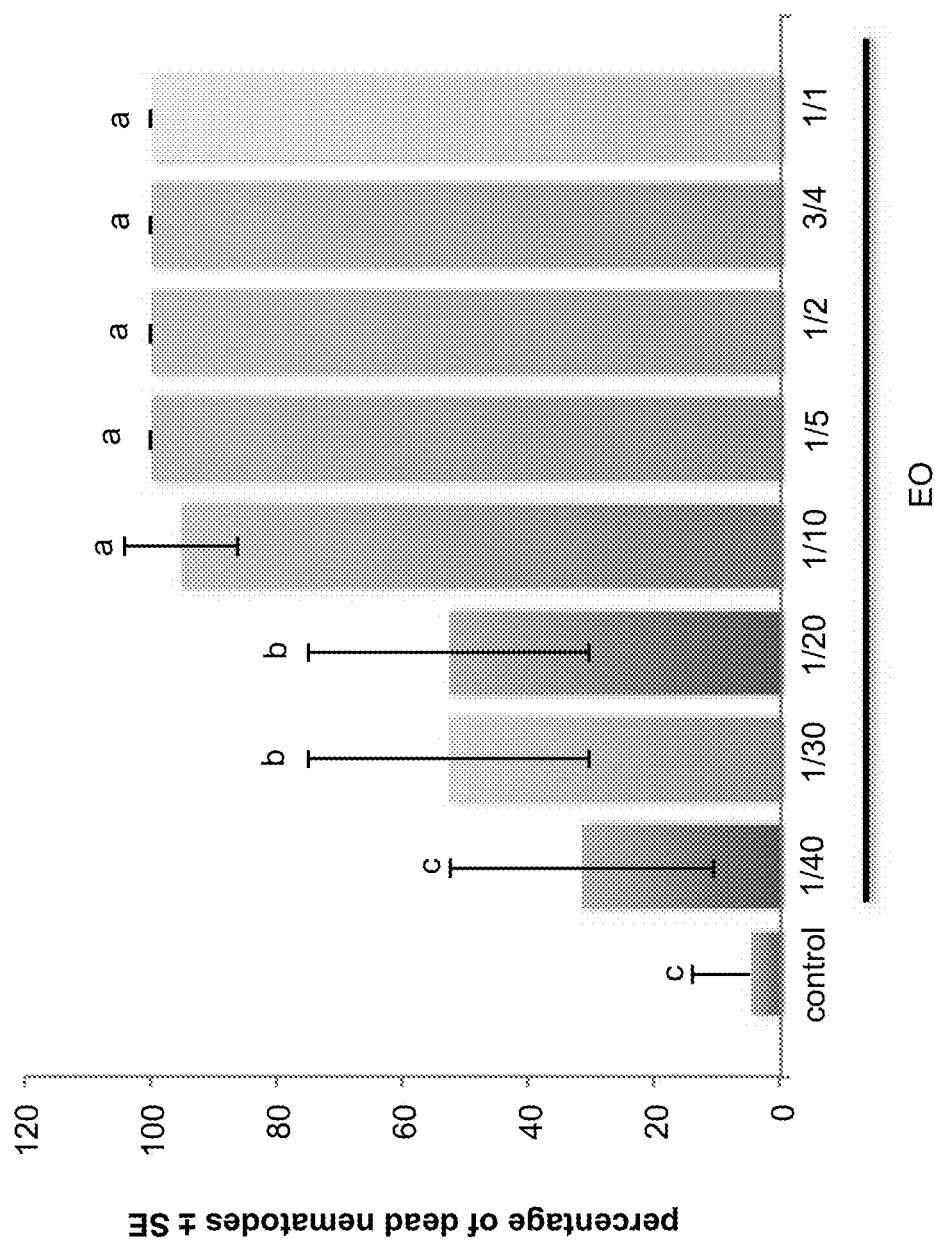
FIG. 9 shows a chart with the percentage of dead Us pathogenic nematodes (*M. incognita*) per treatment after recovery test. ANOVA and Tukey's test were used to analyze the data. Means followed by the same letter are not significantly different (p-value<0.05).

A gradual increase in nematode mortality was observed with longer exposure times. However, even after only 2 h of exposure, 100% mortality of *M. incognita* was observed at dilutions of 3/4, 1/2, 1/5 and 1/10 (FIGS. 7A-C). At 24 hours, no mortality was observed in the control. Similar results were found when this trial was repeated (FIGS. 8A-D). After 48 h of exposure, 100% nematode mortality was observed regardless of the dilution.

Recovery of *M. incognita*

Figure 10A:
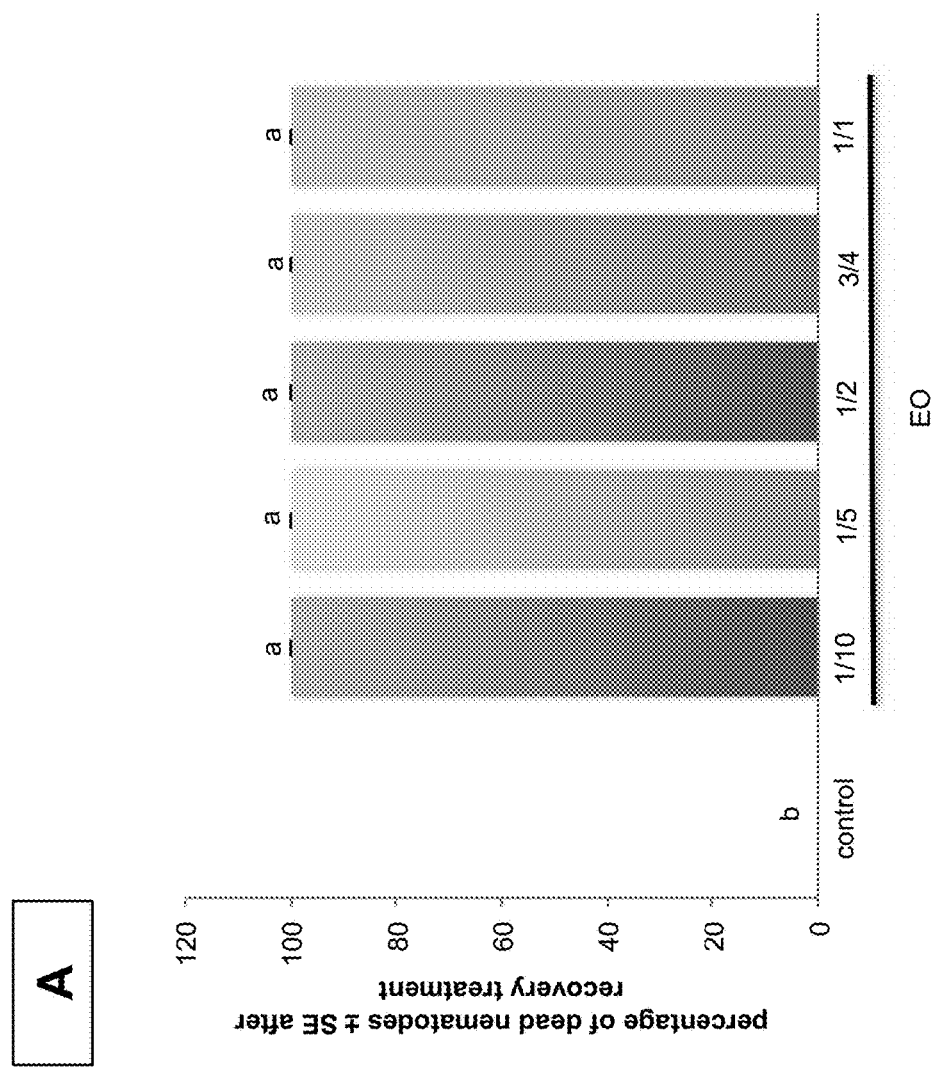
FIGS. 10A-B shows the mortality percentage of Us from *M. incognita* after recovery test. Recovery test was done after 24 hours of treatment (A) and after 48 hours (B). ANOVA and Tukey's test were used to analyze the data. Means followed by the same letter are not significantly different (p-value>0.05).
Figure 10B:
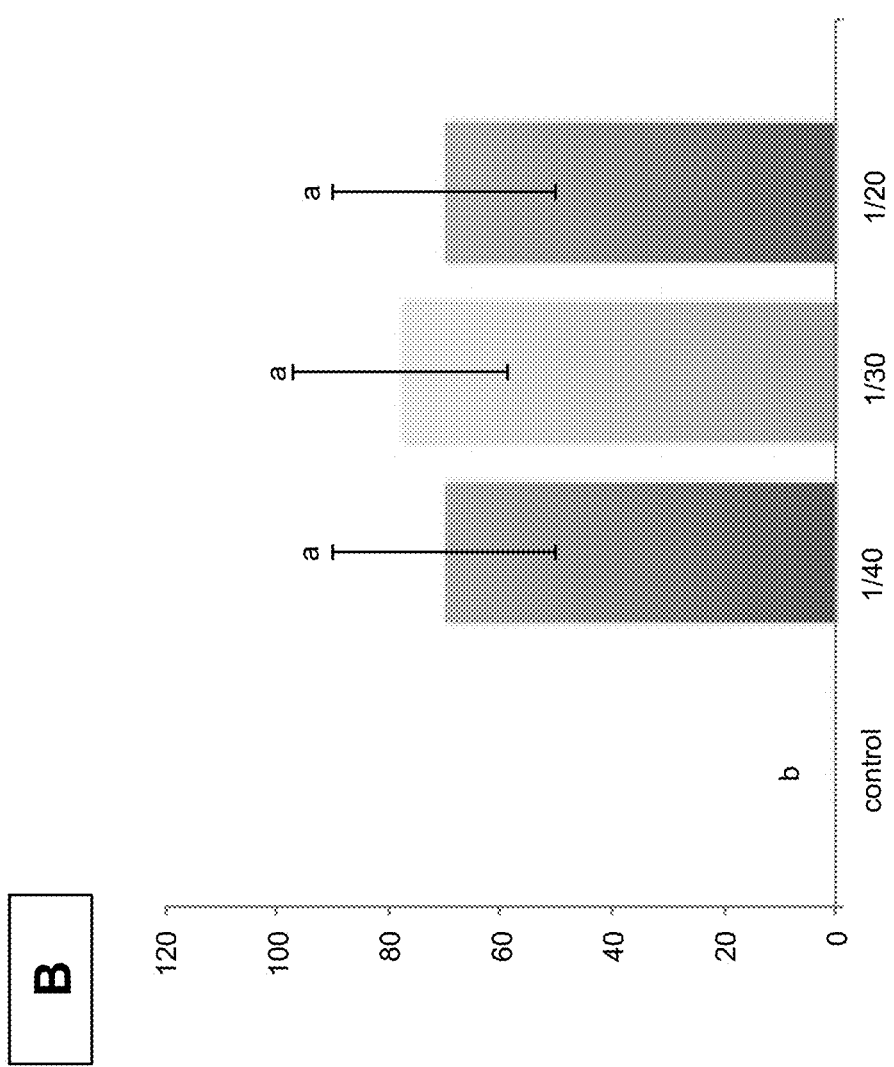

No nematodes recovered after exposure to dilution rates of 3/4, 1/2, 1/5 and 1/10. However, approximately 50% recovery was observed with nematodes exposed to the weaker dilutions (1/20, 1/30 and 1/40). Similar results were obtained when the trial was repeated (FIGS. 10A-B).

Mortality of *S. feltiae*

Figure 11:
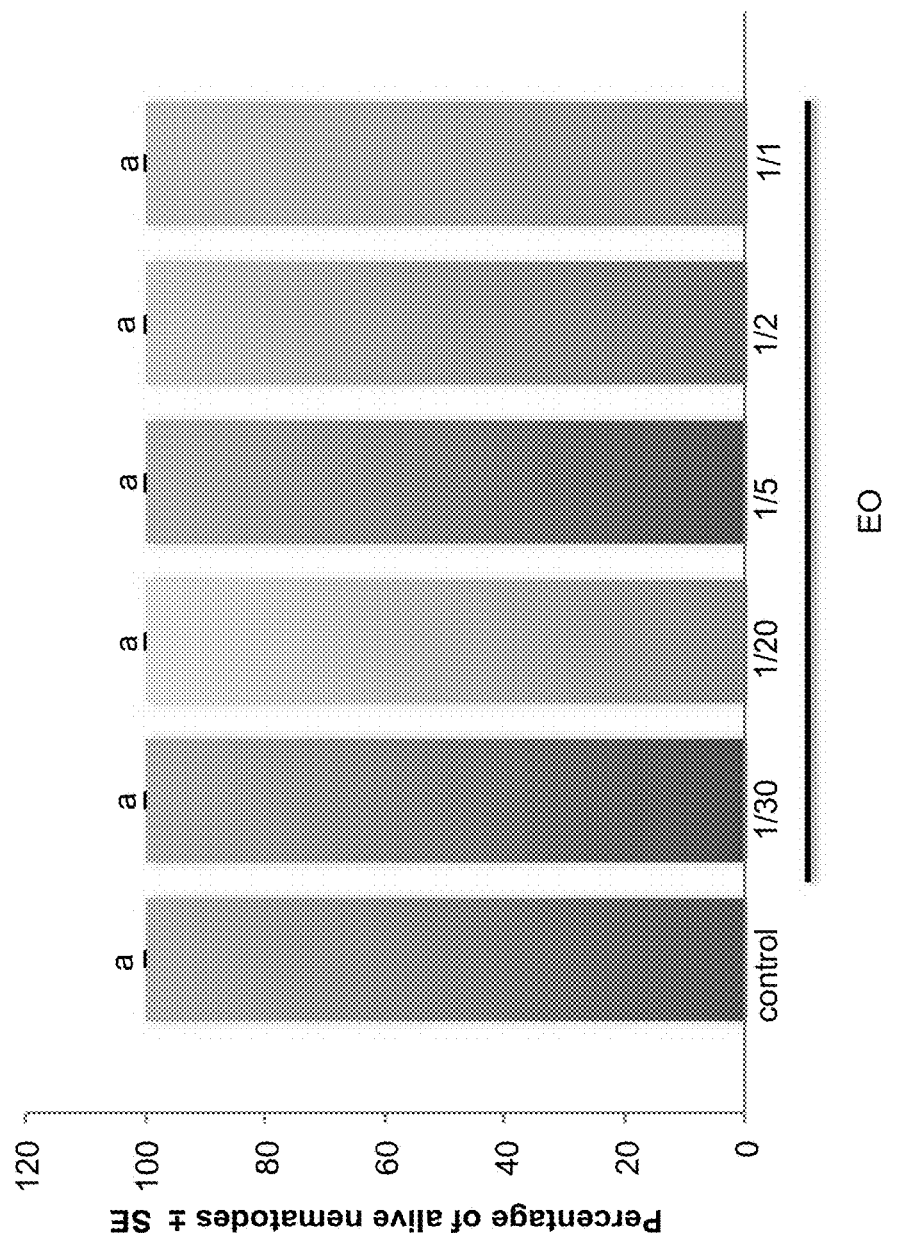
FIG. 11 shows the percentage of living nematodes of *S. feltiae* after 72 hours of treatment incubation. All beneficial nematodes were alive using the different dilutions of EO. ANOVA and Tukey's test were used to analyze the data. Means followed by the same letter are not significantly different (p-value>0.05).

No mortality was observed at any dilution rate regardless of the exposure interval; all the nematodes survive (FIG. 11).

Conclusions

The product EagleOne® has potential as a nematocide. It demonstrated excellent activity against the difficult to kill and very serious root know nematode (*M. incognita*) while demonstrating 100% compatibility with the very important and widely used entomopathogenic nematode, *S. feltiae*.

Test to determine the effectiveness of EagleOne® (EO) Against Infective Juveniles (IJs) of *Meloidogyne incognita* (Plant Pathogenic Nematodes) on Sand Methods All work was done at University of California campus in Davis, Calif., USA. Nematodes were obtained from a laboratory culture maintained in the UC Davis Department of Entomology and Nematology.

The effect of EagleOne® (EO) was tested on infective juveniles (IJs) of *Meloidogyne incognita* on sand. First, we sterilized the sand at 100° C. for 4 hours and 3 grams of sand were added into test tubes. Three different dilutions of EO were evaluated (1/10, 1/5 and 1/1 of EO) and a control was done using only distillated water. We applied 300 µl of each treatment per tube to obtain a 10% of humidity in the sand. Then, 50 IJs of *M. incognita* were added per tube and samples were incubated at 20° C. for 1, 4 and 7 days. After, IJs were extracted by mixing 5 ml of distillated water with the sand; this step was repeated 3 times per sample. Dead and alive nematodes were counted using a microscope and a viability of nematodes were observed by using an eyelash probe. Five replications per treatment were done and a Tukey statistical analysis was performed using JMP software (USA). This experiment was done twice; in the first case we counted the nematodes at day 1 and 4 while in the second time we counted them at day 1 and 7.

Results

Figure 12:
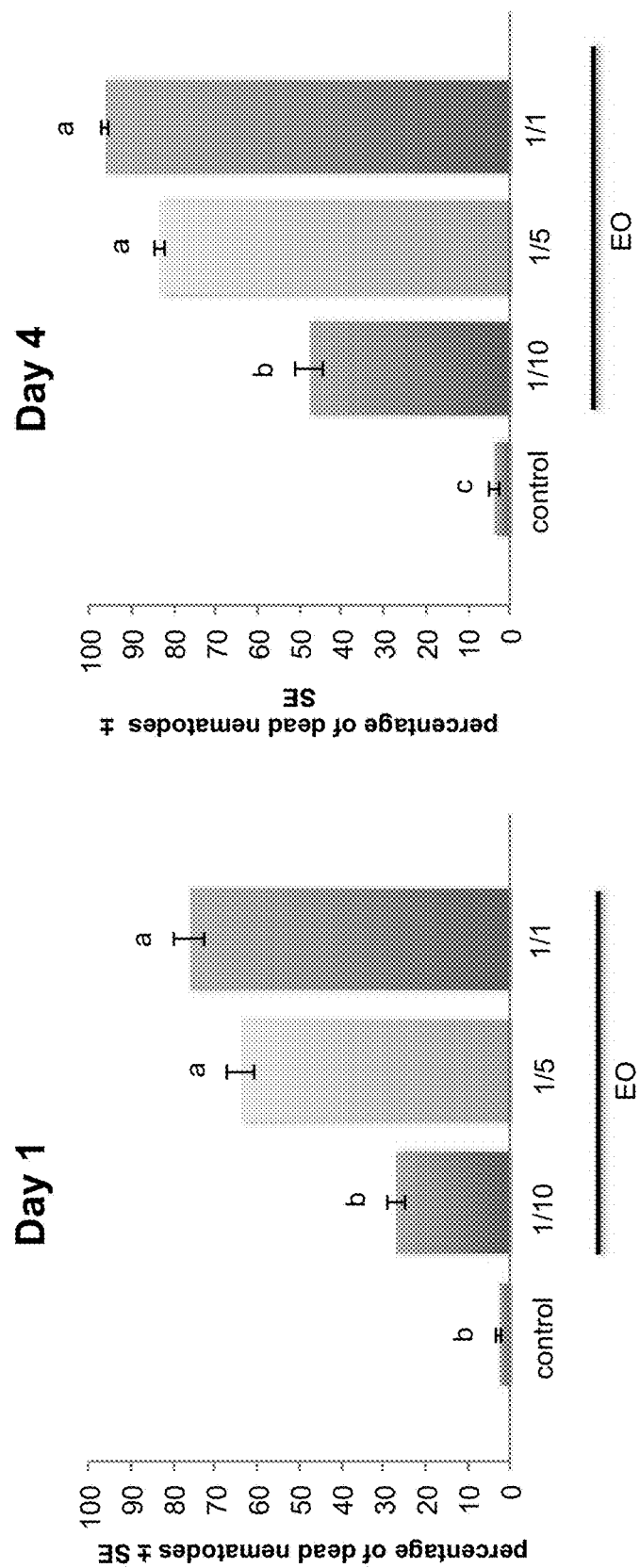
FIG. 12 shows the percent mortality (±SE) of Us of *M. incognita* on sand using different EO dilutions after 1 and 4 days of exposure periods. A Tukey statistic test was performed. Means not connected by the same letter are significantly different (p-value<0.01).

A gradual increase in nematode mortality was observed with longer exposure times using different dilutions of EO. In the first assay, we observed 27, 64 and 76% of mortality when we applied 1/10, 1/5 and 1/1 of EO at day 1 (FIG. 12). These percentages had increased to 48, 83 and 96%, respectively; when the samples were incubated for 3 days more.

Figure 13:
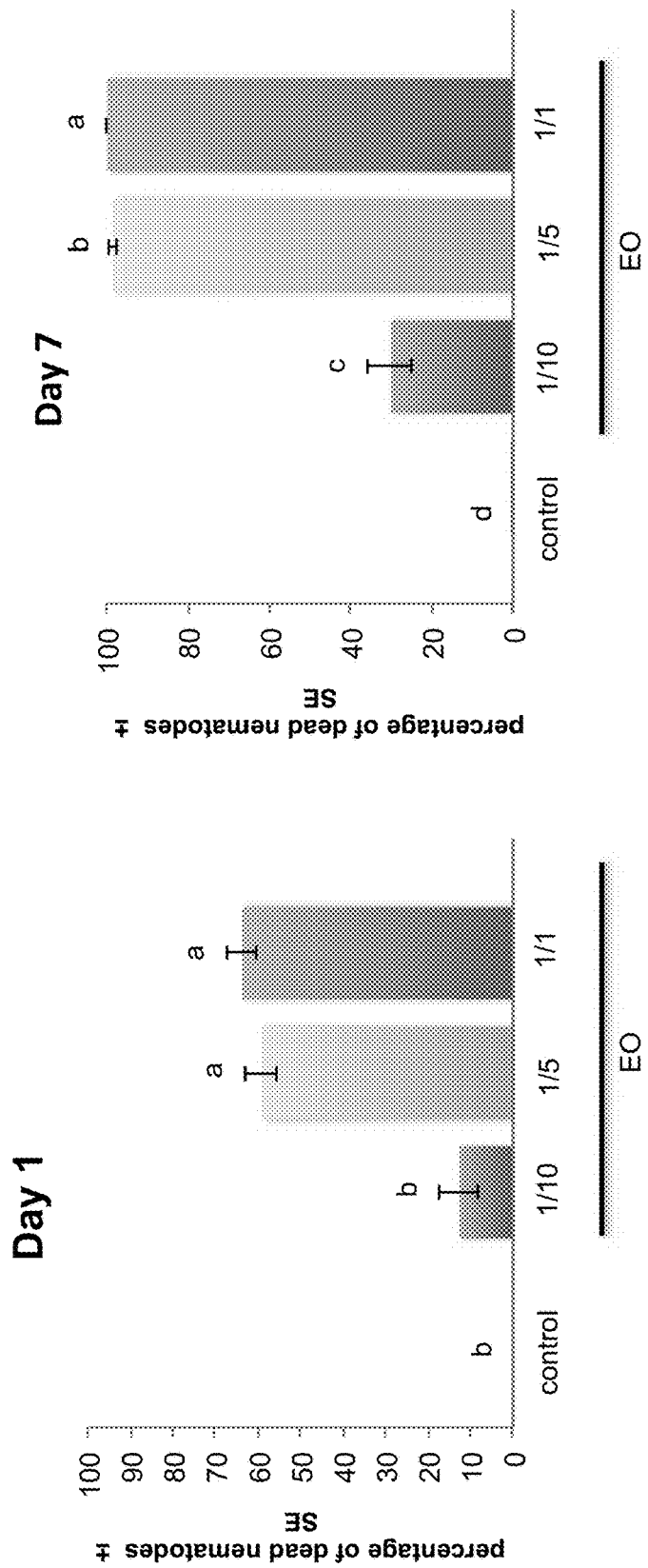
FIG. 13 shows the percent mortality (±SE) of Us of *M. incognita* on sand using different EO dilutions after 1 and 7 days of exposure periods. A Tukey statistic test was performed. Means not connected by the same letter are significantly different (p-value<0.01).
Figure 14:
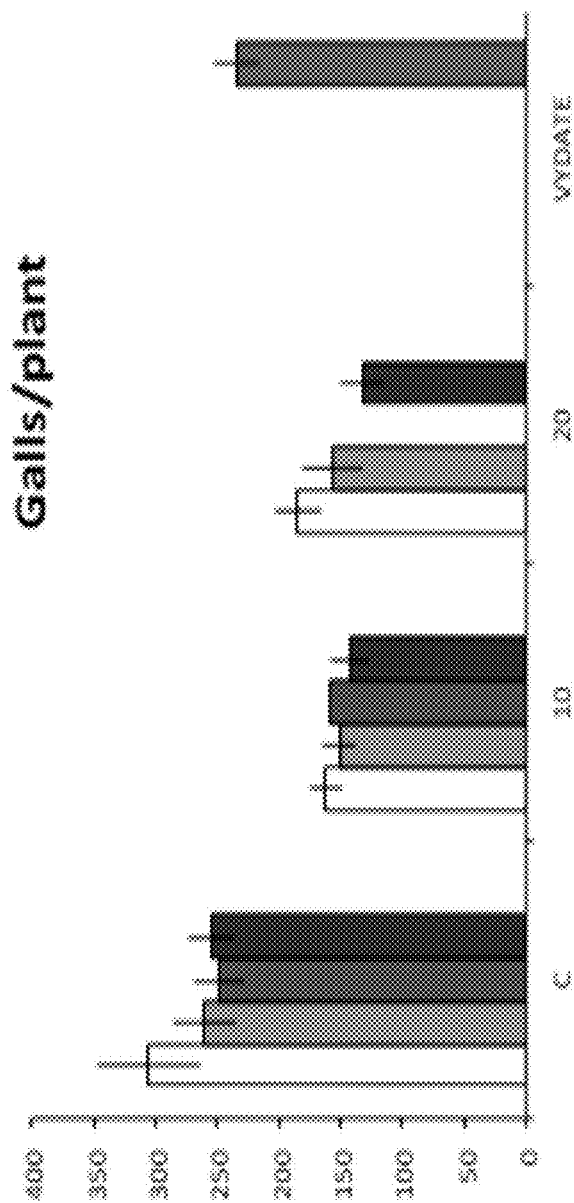
FIG. 14 shows the number of galls per plant after one, two, three applications, progeny and Vydate® concentrations for 10% and 20% EO EO versus control.
Figure 15:
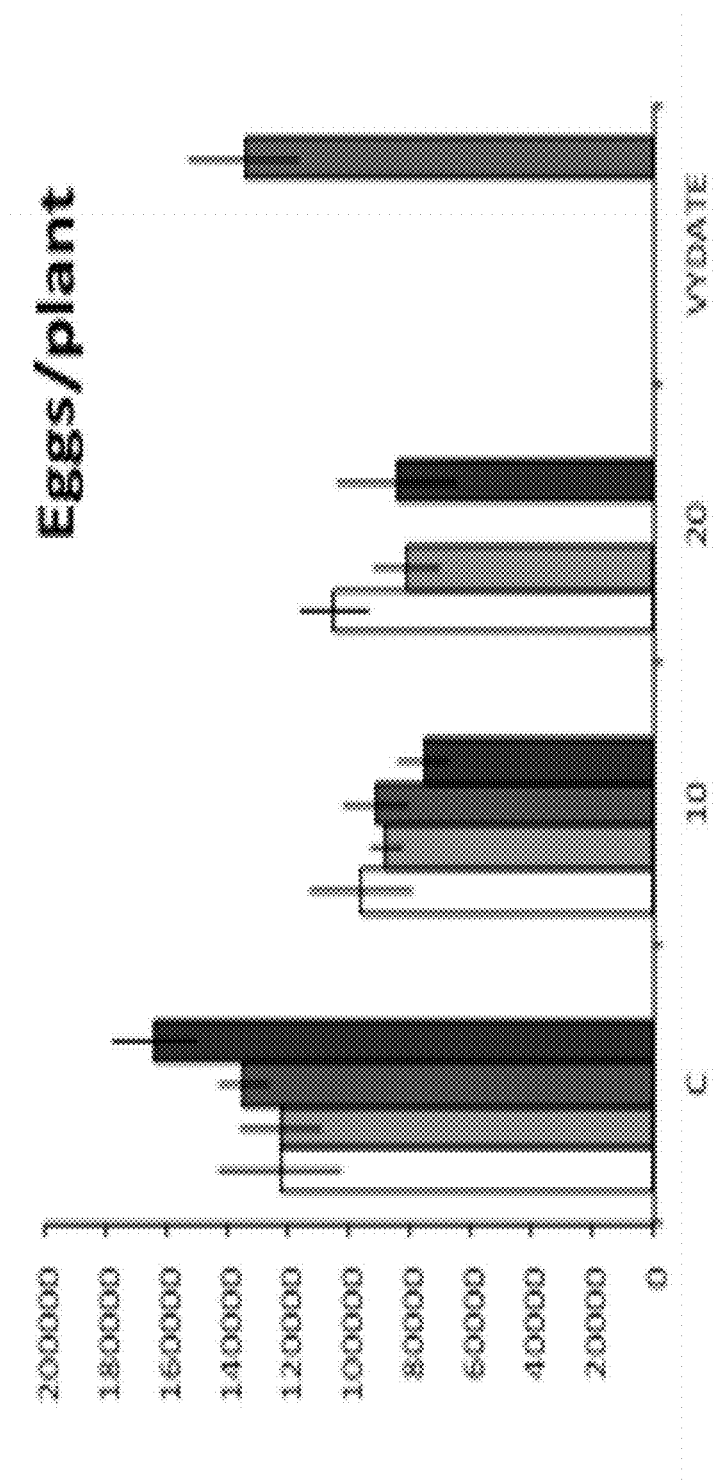
FIG. 15 shows the number of eggs per plant after one, two, three applications, progeny and Vydate® for concentrations 10% and 20% EO EO versus control.
Figure 16:
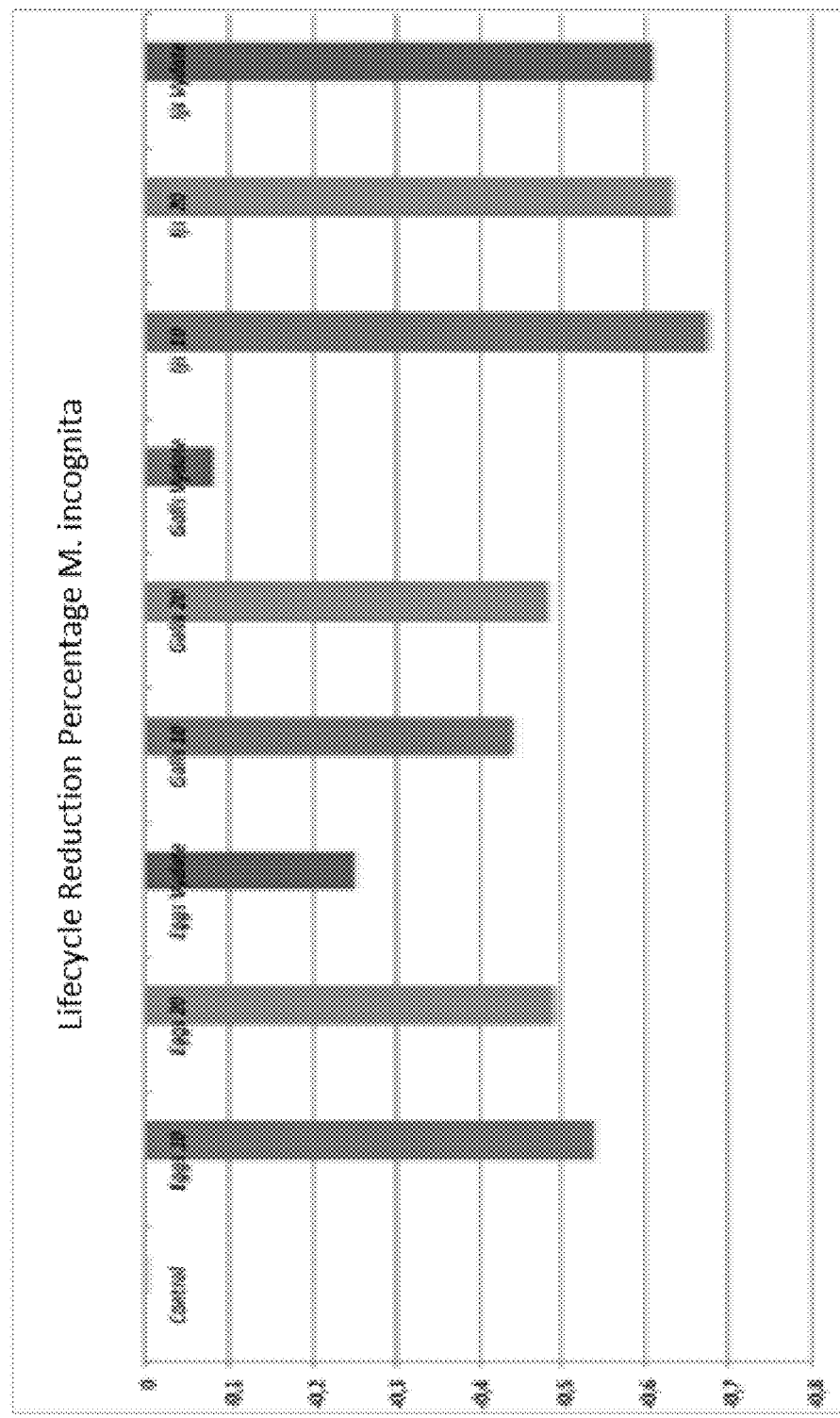
FIG. 16 shows a graphic showing the percentage reduction in eggs, gills and infective juvenile nematodes in both concentrations studied (10 to 20%) compared to the control and Vydate®.

Similar results were found in the second assay. We saw less effectiveness of EO at day 1, but 100% of mortality was observed after one week of treatment when 1/5 and 1/1 EO were applied (FIG. 13).

The following charts show the percent mortality (±SE) of IJs of *M. incognita* on sand using different EO dilutions after 1 and 4 days of exposure periods. A Tukey statistic test was performed. Means not connected by the same letter are significantly different (p-value<0.01).

The following charts show the percent mortality (±SE) of IJs of *M. incognita* on sand using different EO dilutions after 1 and 7 days of exposure periods. A Tukey statistic test was performed. Means not connected by the same letter are significantly different (p-value<0.01).

Conclusions

The product EagleOne® has potential as a nematocide. It demonstrated excellent activity against the difficult to kill and very serous root know nematode (*M. incognita*) on sand after one week of treatment.

Test to Determine the Effectiveness of EagleOne™ as a Nematicide, Evaluating the Decrease in Gills and Eggs of Meloidogyne Incognita in Pots with Soil to 5% Vermiculite.

Methods

The trial was fully done in the campus University of California Davis, Calif., 95616, USA, nematodes Meloidogyne incognita were obtained in culture laboratory Department of Entomology and Nematology.

The effect of EagleOne™ (EO) were analyzed in galls, nematode eggs in soil with 5% vermiculite pots 1 galon.

First land of an area intended for the laboratory for this purpose and sterilized in an oven at 100° C. (in the center of the container with soil) was extracted for three hours, then the earth moved to the greenhouses and mixed with 5% vermiculite the mixture 150 1 gallon pots each were added. Moreover, they were planted and grown tomato seedlings of the variety Rutgers, which are highly susceptible to infection by nematodes. seedlings were transplanted to the pots and allowed to set for 7 days, watering pots was automatic, watering twice a day with a flow of 3 ml/min and the greenhouse temperature was fixed at 26° C. to help the infection. The pots were infected by adding about 1000 infective juveniles nematodes around the plant divided by 4 points and 5 cm deep. The degree of infection 22 days after it is checked and decided to make the first application of the product on 25 after inoculation. The experiment is divided into:

First application, where doses (10% EO, 20% EO and Absolute control) were evaluated in 12 pots each, performing sampling on 14.

Second Application, where dose (10% EO, 20% EO and Absolute control) were evaluated in 12 pots each, and a second application is performed on the 7th, performing sampling 14 days after this.

Third Application, where dose (10% EO and Absolute control) were evaluated in 12 pots each performing a second application on day 7 and a third application on 14, performing sampling 12 days after this.

Progeny, where dose (10% EO, 20% EO and Absolute control) in 12 pots were evaluated and monitored every 25 days after, was used as positive control commercial nematicide (Vydate® DuPont) in the dose recommended by the manufacturer for tomatoes, 10 lt/Ha and water control in 12 pots each, sampling was done 25 days after application.

The plants were processed by extracting it completely, a homogeneous soil sample for counting of infective nematode juveniles was saved, the root is washed in running water for counting gills and then the eggs were extracted by the method of chlorine, eggs They were counted under microscope.

Results

To counts galls first application, a decrease of 40% to 10% EO dose and 47% to 20% EO dose for two applications the range of effectiveness is maintained with percentages of 40% to 10 notes % EO and 42% to 20% EO in three applications results bordering the 37% reduction, to evaluate the reduction of guts with Vydate®, this only reaches 8%. In assessing the progeny data we can see a 44% reduction CON10% EO and 48% with 20% EO The following chart shows the number of galls per plant after one, two, three applications, progeny and Vydate® concentrations for 10% and 20% EO EO versus control (FIG. 14).

Egg counts for an application shows a reduction of 15% to 10% EO and 22% to 20% EO values that improve the experiment with two applications where values of 34% to 10% EO and observed 28% to 20% EO, the experiment with three applications yields a decrease of 38% compared to control. Vydate® effect on reducing *M. incognita* eggs is 25%. The greatest reduction in number of eggs per plant were observed in the progeny trials where it reaches 54% using 10% EO and 49% with 20% EO. (FIG. 15)

The following chart shows the number of eggs per plant after one, two, three applications, progeny and Vydate® for concentrations 10% and 20% EO EO versus control.

Statistical analyzes show that with 1 application both EO concentrations of 10% ($P<0.01$) and 20% EO ($P<0.02$) significantly reduce the formation of galls compared to control, with two product applications both concentrations significantly reduce the guts ($P<0.01$ in both cases) egg reduction versus control was significant ($P=0.03$) only in the concentration 10% EO. In the test with three applications 10% EO concentration shows that eggs and guts were reduced significantly ($P<0.01$) compared to control. Progeny tests show that both concentrations significantly reduce galling, eggs and juveniles compared to control nematodes. ($P=0.01$). (FIG. 16).

The following chart shows a graphic showing the percentage reduction in eggs, gills and infective juvenile nematodes in both concentrations studied (10 to 20%) compared to the control and Vydate®.

Conclusions

EagleOne™ product acts as a powerful nematicide *Melodogyne incognita* species with light soil in pots, achieving significant reductions galls and eggs levels above chemical nematicide, Vydate®.

Use concentration was defined in a dilution of 10% EagleOne™ with a single application.

Bleach Extraction of Meloidogyne
Modified from:
An advanced treatise on *Meloidogyne* Vol II Methods. Eds. K R Barker and J N Sasser. North Carolina State University Graphics. 1985.

1. Wash all excess dirt off of infected tomato roots.
2. Cut tomato roots into 1-2 cm segments.
3. Rub roots gently together in a beaker of 1% bleach solution for 1 min.
4. Quickly pass bleach solution through a 20 mesh sieve nested over a 100 mesh and 400 mesh sieve, to collect eggs. (note: sieves should be wet).
5. Rinse contents of 400 mesh sieve under cold water for 2 minutes.
6. Rinse roots with water over both sieves for 2 minutes.
7. Place contents of 500 mesh sieve in Baermann funnel filled with water.
8. Immediately wash sieves, rinse with DI water and put away.
9. Collect hatched IJs at 24 and 48 hr and place in 15 C.

*Note: This method can also be used to extract Meloidogyne eggs from infected Arabidopsis roots. To measure infection levels only eggs need to be counted, eliminating steps 7-9. Rinse eggs caught in the 500 mesh sieve into a container, then count. Eggs can be held at 15 C until counted.

Evaluation on the Control of Phytoparasitic Nematodes Using the Product Eagle One Introduction Grapevines in Chile are farmed under various soil and climate conditions, and vines are constantly subjected to the pressures of diverse pathogens. Soil pathogens include phytoparasitic nematodes from distinct genera, such as Xiphinema and *Meloidogyne*, among others. These nematodes can significantly impact grapevines, causing, for example, damaged roots, lowered production, and pathogen susceptibility.

Objective

The objective of this study was to evaluate the effects of the product EAGLE ONE in the control of phytoparasitic nematode populations at a functioning wine-grape vineyard in the La Pintana community (Santiago, Chile).

Materials and Methods

This study was performed at a vineyard belonging to the Faculty of Agricultural Sciences of the Universidad de Chile. The vineyard is located in the La Pintana community (Santiago, Chile), and the evaluated sector presented the following characteristics:

Sector: Vildes & Parronal
Variety: Chardonnay
Planting year: 1992
Density: 2.5×1.2 m
Rootstock: Own-rooted massal
Watering system: Dripline
Distance between drips: 0.85 m For assessments, a single dose of EAGLE ONE was distributed in a sector with a high presence of phytoparasitic nematodes. The results of this assessment were compared against treatments with a chemical nematicide (Vydate® L) and a control without any treatment (Table 1).

TABLE 1

Treatment descriptions.

| TREATMENT | DESCRIPTION | DOSE |
|---|---|---|
| 0 | Control (Only water) | |
| 1 | EAGLE ONE | 10% concentration |
| 2 | Vydate ® L (Chemical) | 10 L/ha |

Plant and dripline selection. Rows were selected for analyses based on plant homogeny in regard to vigor and health. The selected plants demonstrated normal vigor. The closest dripper hole to each selected plant was selected for assessments.

Soil sampling and nematode analyses. Sampling was performed with shovels, taking soil and root samples from the area watered by each selected dripper. Samples were taken prior to application and 20 days post-application. For nematode analysis in the soil samples (250 cm3), Cobb's sieving method was used together with a Baermann funnel (Christie and Perry, 1951). The obtained material was filtered for 48 h. Nematodes were identified and counted using a stereoscopic magnifying glass. The quantity of individuals by genus was recorded.

Treatment applications. Applications were applied to the selected plants using the drenching method. Specifically, 40 L of water were applied to each treated sector, thus simulating 2 h of watering. For initial assessments and the control group, only water was used. For treatment groups, EAGLE ONE (4 L product/40 L water) or Vydate® L (10 L/ha) were applied to plants using the drenching procedure. The dates of each experimental stage are indicated in Table 2.

TABLE 2

Sampling and treatment dates.

| ACTIVITY | DATE |
|---|---|
| Pre-treatment sampling | Mar. 18, 2016 |
| Treatment application | Mar. 18, 2016 |
| Post-treatment sampling | Apr. 18, 2016 |

Experimental Design

Assays were performed to evaluate the effects of applying a dose of EAGLE ONE to phytoparasitic nematodes. A Completely Randomized Design was implemented, using three treatments, each with six repetitions. Treatments were applied to the soil areas wetted by each selected dripper. Each experimental unit corresponded to one plant.

Data were logarithmically transformed using the formula Log(x+1), thereby adjusting populations to a normal distribution curve for posterior Analysis of Variance (ANOVA). If statistically significant differences were detected via ANOVA, data were posteriorly assessed using Fisher's Least Significant Difference test (p<0.05) to establish averages. All statistical analyses were performed using the InfoStat v.2013 statistical software.

The percentages of effective population control achieved by each treatment were calculated as a function of nematode population variances as compared to initial populations. Variations in reproductive rate between treatment groups as compared to control (i.e. water only) counterparts were calculated according to Equation (1):

$$(1-(TR\ trat/TR\ test))*100 \tag{Eq. 1}$$

Where TR test is the reproductive rate of the control group and TR trat is the reproductive rate of the treatment group.

Results

According to the obtained results, most nematode populations were identified as Xiphinema index. Notably, this nematode species is of primary agricultural concern as it is the dominant species affecting the agricultural sector.

A second analysis was also performed collectively considering the nematode genera Helicotylenchus, Paratylenchus, and Pratylenchus. Although not of primary agricultural concern, these nematode populations were considered due to presenting high frequencies and distributions in the assessed plants.

Nematodes from the genera Mesocriconema and Zygotylenchus were also recorded, but since populations were not found in all replicas, these genera were excluded from posterior analyses. Other infrequently detected genera included Criconema, Meloidogyne, Trichodorus, and Tylenchulus (FIG. 17).

Significant differences were obtained in reproductive rate between treated X. index populations, the most homogenously distributed species in the assessed sector. Both treatment groups (EAGLE ONE and Vydate® L) evidenced reduced final X. index populations as compared to initial X. index populations. As compared to the control group (i.e. water only), EAGLE ONE reduced populations by ≈50% while Vydate® L reduced populations ≈60%.

Regarding the collective assessment of the Helicotylenchus, Paratylenchus, and Pratylenchus genera, no significant differences were found in treatment groups as compared to initial populations. While not significant, treatment groups as compared to the control condition did evidence some degree of population control. Without doubt, these nematode genera presented the greatest population variations.

Study on the Control of Phytoparasitic Nematodes in Grapevines—Evaluation of EAGLEONE™ Plus Objective The objective of this study was to evaluate the effect of the microbe-derived product EAGLEONE™ on the mortality of phytoparasitic nematodes associated with adult grapevines.

Materials and Methods.

This study was performed in 19 year-old Cabernet Sauvignon variety grapevines kept at the Experimental Center of the Universidad de Chile, Ave. Santa Rosa 113015, La Pintana, Metropolitan Region, Chile.

The most relevant crop characteristics were as follows:
Sector: vineyards
Variety: Cabernet Sauvignon
Density: 3*1 m/3.333 plants/ha
Rootstock: Freedom
Watering: drippers 4 L/hour, 2 drippers/plant
Distance between drippers: 0.60 m
Planting year: 1996
Soil type: Alluvial soil, Freedom The following treatments were implemented:
1. 2% EagleOne™
2. 5% EagleOne™
3. 10% EagleOne™
4. Rugby 200 CS nematicide at a dose of 15 L/ha
5. Untreated control The treatments were applied on Jun. 12, 2015, by drenching each plant with 8 L of solution. This amount of solution was equivalent to injecting each treatment into the soil for 1 h through the watering lines.

A random experimental design was used, with five treatment groups and four replicates of each group. Each repetition consisted of a land plot with three plants.

The treatments were evaluated by analyzing variations between the initial (Pi) and final (Pf; 30 days of treatment) nematode populations. To estimate treatment efficiency, the most aggressive and most dense nematode species were assessed. Nematological analysis of the soil samples was used to determine the quantity of mobile nematode stages. For this, the soils samples were sifted and then filtered for 48 h in a Baermann funnel. Nematode stages were identified using a 50× stereoscopic magnifying glass.

Using the initial and final population data, the reproduction rate was determined (i.e. Pf/Pi), and this value was assessed using analysis of variance. In cases where significant differences existed ($P \leq 0.05$), a Tukey's post-hoc test was applied to separate averages, with the same confidence interval.

Results

Population, reproductive, and treatment data are presented in FIG. 19. The efficiency of the implemented treatments was determined based on populations of the ectoparasitic nematode Xiphinema index, which was chosen as it was the densest and stablest nematode population during experimental procedures. Other nematode genera were inconsistently detected at the land plots and were not considered in final analysis.

In the three groups treated with the nematode-control products, the quantity of X. index decreased by 33.9 and 35.7% for EagleOne™ concentrations of 2, 5 and 10%, respectively. However, the degree of difference between these treatment methods was insignificant in statistical terms, partly due to natural variations in density and to a heterogeneous distribution profile.

On the other hand, the phosphorylated nematicide Rugby 200 CS produced a greater average decrease in nematode populations, showing statistically significant differences as compared to the control group.

What is claimed is:

1. A nematode killing composition consisting essentially of nematode killing amounts of gluconacetobacter malus and vitas vinifera.

* * * * *